(12) United States Patent
Yoshimi et al.

(10) Patent No.: US 6,450,957 B1
(45) Date of Patent: Sep. 17, 2002

(54) RESPIRATORY DISEASE MONITORING SYSTEM

(75) Inventors: Tomohisa Yoshimi, Gamagori; Kenichi Yanai, Nisshin; Yoshifumi Nishida, Tsukuba, all of (JP)

(73) Assignee: Denso Corporation, Kariya (JP)

( * ) Notice: Subject to any disclaimer, the term of this patent is extended or adjusted under 35 U.S.C. 154(b) by 112 days.

(21) Appl. No.: 09/612,557

(22) Filed: Jul. 7, 2000

(30) Foreign Application Priority Data

Aug. 2, 1999 (JP) ............................................. 11-218486

(51) Int. Cl.[7] ................................................. A61B 5/00
(52) U.S. Cl. ...................... 600/309; 600/595; 600/587; 600/534; 600/322
(58) Field of Search ................................ 600/322–324, 600/534–536, 587, 595, 309

(56) References Cited

U.S. PATENT DOCUMENTS

| | | | |
|---|---|---|---|
| 4,765,340 A | * | 8/1988 | Sakai et al. .................. 600/324 |
| 5,199,424 A | * | 4/1993 | Sullivan et al. .............. 128/204 |
| 5,385,144 A | | 1/1995 | Yamanshi et al. |
| 5,671,733 A | * | 9/1997 | Raviv et al. ................. 600/301 |
| 5,964,720 A | * | 10/1999 | Pelz ............................ 600/595 |
| 5,989,193 A | * | 11/1999 | Sullivan ...................... 600/534 |
| 6,011,477 A | * | 1/2000 | Teodorescu et al. ......... 340/573 |

FOREIGN PATENT DOCUMENTS

| | | |
|---|---|---|
| JP | 63-158040 | 7/1988 |
| JP | 05200001 | 8/1993 |
| JP | 11-504840 | 5/1999 |

* cited by examiner

*Primary Examiner*—Eric F. Winakur
*Assistant Examiner*—Matthew J. Kremer
(74) *Attorney, Agent, or Firm*—Law Offices of David G. Posz

(57) ABSTRACT

A respiration monitoring system monitors the state of disorder of the respiratory system of a sleeping patient based on the detection of respiratory body movement without the need of putting sensors directly on the patient's body. The system includes weight sensors that produce weight signals attributable to the patient's respiratory body movement. From weight signals having a frequency band of respiration, a respiratory body movement signal is produced, and the fall of blood oxygen saturation which occurs at obstructive apnea of the sleeping patient is determined based on the variation pattern of the amplitude of respiratory body movement signal. The occurrence and frequency of the fall of blood oxygen saturation are displayed on a display unit.

25 Claims, 6 Drawing Sheets

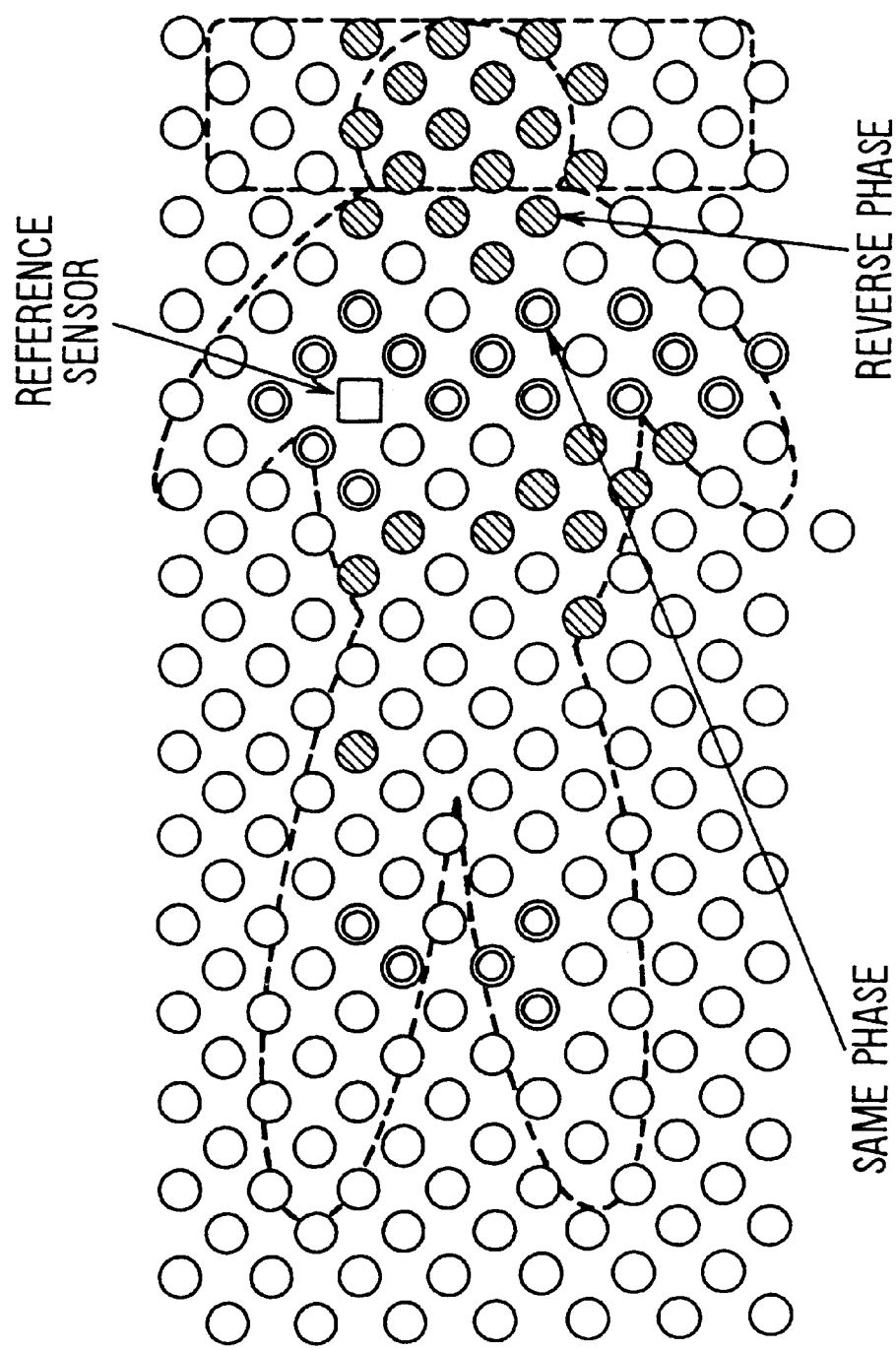

RESPIRATORY DISEASE MONITORING SYSTEM

CROSS-REFERENCE TO RELATED APPLICATION

The present invention is related to Japanese patent application No. Hei. 11-218486, filed June Aug. 2, 2000, the contents of which are incorporated herein by reference.

FIELD OF THE INVENTION

The present invention relates to a respiration monitoring system, and more particularly to a respiration monitoring system capable of monitoring the state of disorder of the patient's respiratory system during sleep.

BACKGROUND OF THE INVENTION

A conventional medical system for diagnosing a respiratory disease of a sleep apnea syndrome is shown in FIG. 7. Here, this system 100 has an air flow sensor 101, a chest/abdominal movement sensor 102, a snore sensor 103, a body attitude sensor 104, a blood oxygen saturation sensor 105, and a data recorder 106. These sensors 101–105 are put on the patient's body during sleep. The data produced by the sensors is recorded by the data recorder 106.

The recorded data is sent by off-line transfer from the data recorder 106 to an external data analyzer 107, by which the data is analyzed for the diagnosis of respiratory disease. In the diagnostic procedure, the distribution of blood oxygen saturation is first examined, and if a disease is suspected, the patient undergoes more precise inspections based on the data provided by the remaining sensors.

However, for diagnosis as shown in FIG. 7, it is necessary to put many sensors 101–105 on the patient's body during sleep. Therefore, it is not only awkward for the patient to wear these sensors 101–105 with lead wires during sleep, but the sensors must be removed and the patient must be turned over. The present invention was developed in light of these drawbacks.

SUMMARY OF THE INVENTION

It is therefore an object of the present invention to provide a respiration monitoring system which is capable of monitoring the state of disorder of the patient's respiratory system during sleep based on detecting body movement caused by respiration, and without requiring the sensors to be placed directly on the patient's body.

It is a further object of the present invention is to provide a respiration monitoring system that is easily used at home for monitoring the patient's respiratory system, and is useful for the primary care of sleep apnea syndrome.

Further areas of applicability of the present invention will become apparent from the detailed description provided hereinafter. It should be understood that the detailed description and specific examples, while indicating preferred embodiments of the invention, are intended for purposes of illustration only, since various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings, wherein:

FIG. 6 is a graphical view of an operation according to the present invention;

FIG. 8 is a magnified view of a portion of the graphical view in FIG. 4 according to the present invention.

DETAILED DESCRIPTION OF THE PREFERRED EMBODIMENTS

Figure 1:
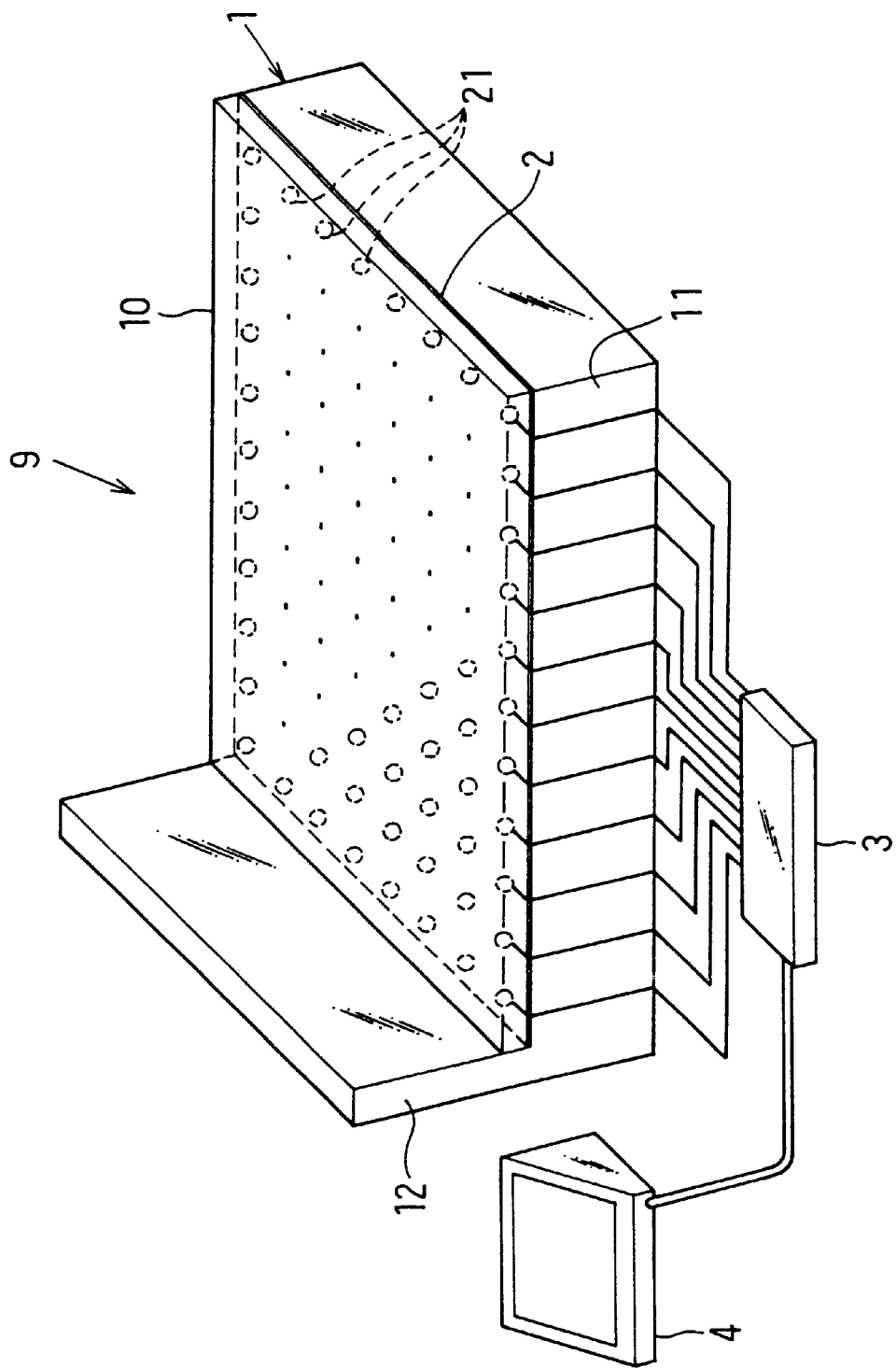
FIG. 1 is a perspective view of the respiratory disease monitoring system according to a first embodiment of the present invention.

FIG. 1 illustrates an arrangement of the respiratory disease monitoring system according to a first embodiment of the present invention. Here, a monitoring system 9 includes a sensor sheet 2 positioned beneath a sleeping pad 10 on a bed 1, a controller 3, and a display unit 4. Display unit 4 displays the frequency of respiration and the frequency of falling blood oxygen saturation of the sleeping patient.

Bed 1 is made up of a frame 11, on which the pad 10 is placed, and a headboard 12 that stands at one end of the frame 11. The sensor sheet 2 has a number of pressure sensitive elements 21 (210 elements in this embodiment) arranged at a constant interval, which vary in electric resistance in response to the weight applied thereto. In the present invention, these elements decrease in resistance with weight. Each pressure sensitive element 21 has a flow of electric current that varies in response to the change in resistance. Accordingly, pressure sensitive element 21 detects weight according to current magnitude.

Figure 2:
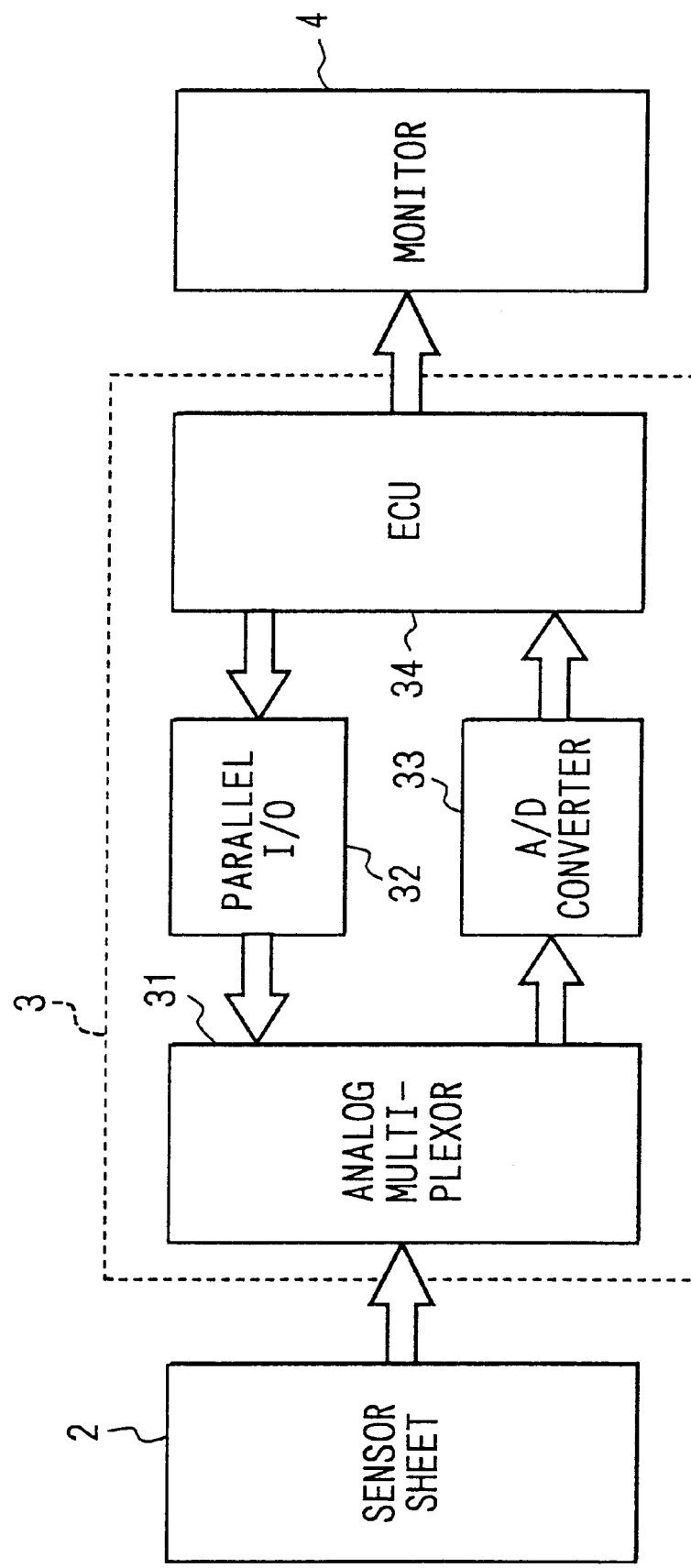
FIG. 2 is a block diagram showing the circuit arrangement of a monitoring system according to the present invention.

Referring to FIG. 2, the controller 3 includes a multiplexer 31, a parallel I/O 32, an A/D converter 33, and an ECU 34. The ECU 34 supplies an element switching signal to the multiplexer 31 through parallel I/O 32. The multiplexer 31 also selects a weight signal from a pressure sensitive element 21 sequentially and feeds the signal through the A/D converter 33 to the ECU 34. Weight signals from the 210 pressure sensitive elements 21 are fed to the ECU 34 at a frequency of about 70 Hz in this embodiment.

ECU 34 calculates a patient's frequency of respiration and the frequency of the fall of blood oxygen saturation based on the input weight signals. ECU 34 delivers the calculated results to the display unit 4. The display unit 4 displays the frequency of respiration and the frequency of the fall in blood oxygen saturation numerically or graphically along a time axis.

This arrangement does not require a sleeping patient to wear sensors, and allows determination, during ordinary life, of the frequency of respiration and the frequency of the fall of blood oxygen saturation during sleep.

Figure 4:
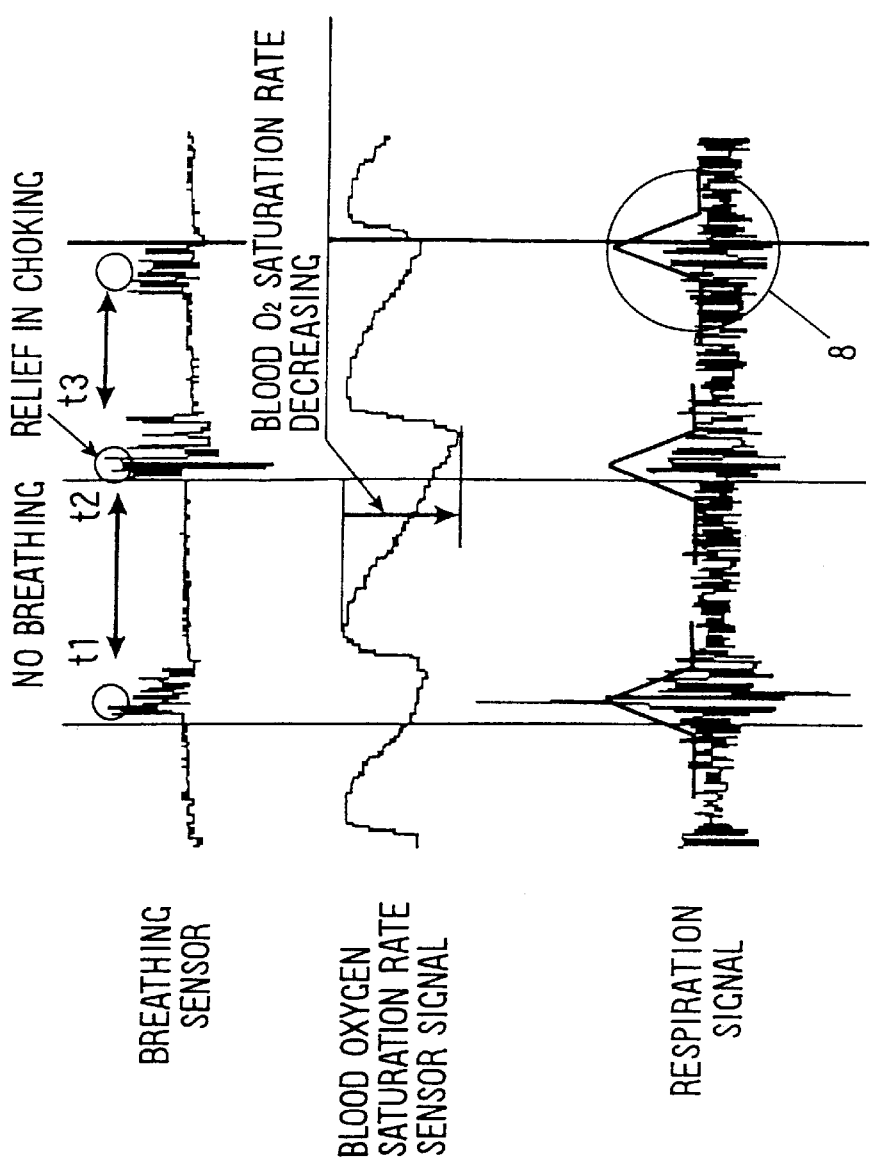
FIG. 4 is a graphical view illustrating an operation according to the present invention.

Next, referring to the clinical data shown in FIG. 4, detection of the fall of blood oxygen saturation is explained. FIG. 4 shows the signal waveforms resulting from measurement for a patient of obstructive sleep apnea. The signals are produced by respiration monitoring system 9 and medical devices (an air flow sensor placed on the nose of the patient and a blood oxygen saturation sensor put on the finger of the patient).

The respiratory body movement signal indicates the vertical movement of the patient's diaphragm during the period from t1 to t2, whereas the air flow signal does not vary in this period. These signal waveforms suggest the state of obstructive apnea, in which the patient's throat is choked due to the relaxation of throat muscle or the like during sleep and air is not inhaled into the lung even with the exertion of respirative motion (vertical movement of the diaphragm). The obstructive apnea lasts until the blood oxygen saturation falls down to the critical level of vitality (time point t2).

When the blood oxygen saturation falls down to the critical level, the patient automatically awakes temporarily, and is quickly relieved of throat choking. At this time, the patient breathes very deeply, which is indicated by a temporary increase in the amplitude of the air flow signal and the respiratory body movement signal of the inventive monitoring system (period from t2 to t3).

Thereafter, blood oxygen saturation returns to its normal level in a short time. The patient falls asleep again, and once again has obstructive apnea. This cycle is repeated.

Figure 5:
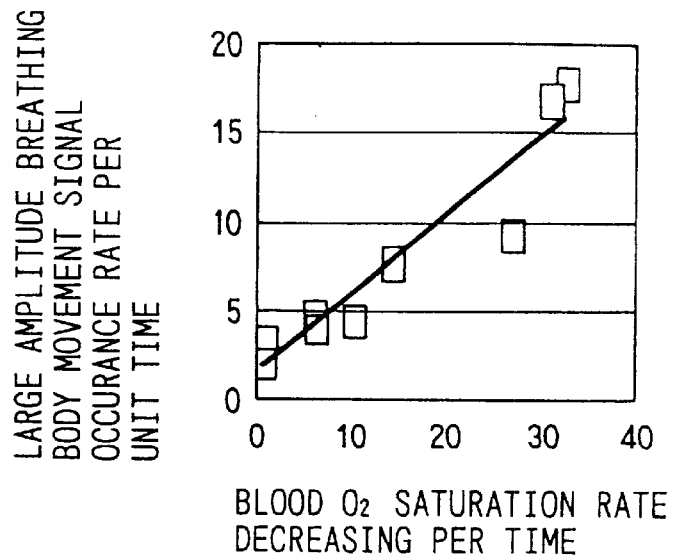
FIG. 5 is a graphical view describing an operation according to the present invention.
Figure 7:
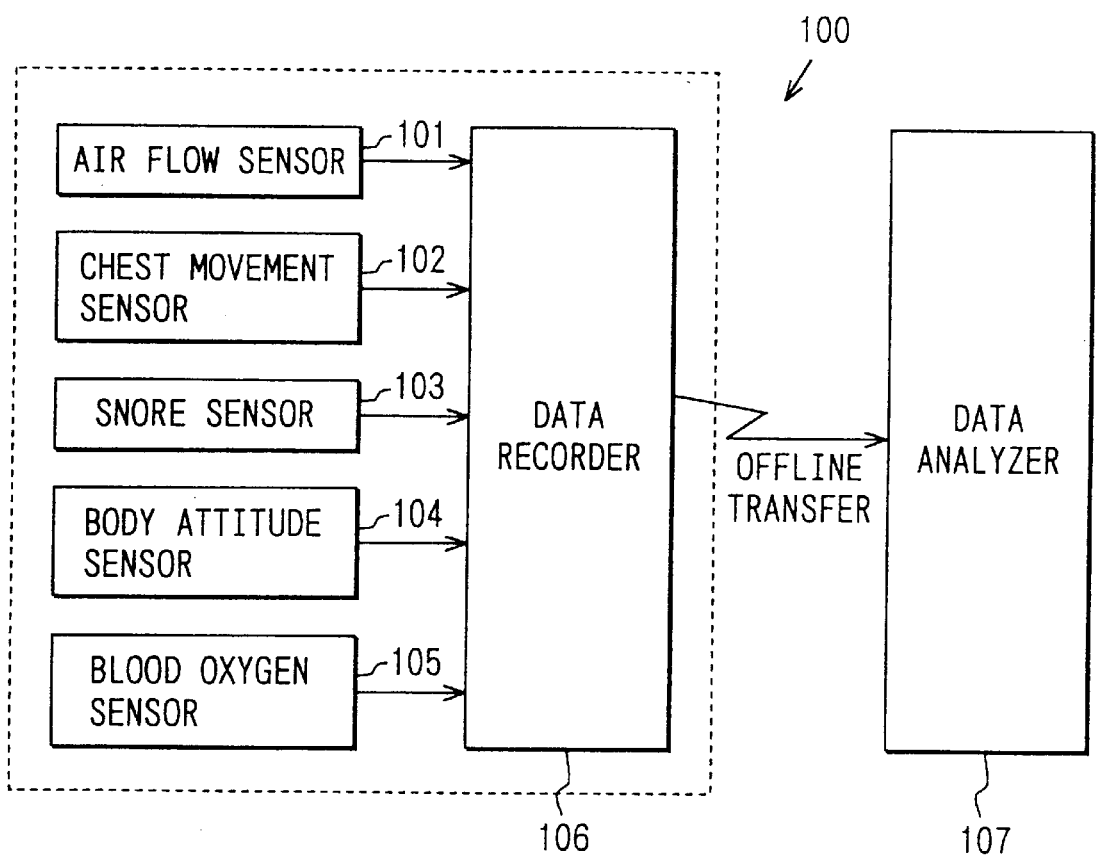
FIG. 7 is a block diagram showing in brief the conventional respiratory disease monitoring system according to the prior art.

This clinical data reveals a definite correlation between the frequency of the occurrence of respiratory body movement signals having large amplitudes detected by the inventive monitoring system and the frequency of the fall in blood oxygen saturation. For example, an actual clinical test revealed a correlation coefficient of 0.97 between the frequency of respiratory body movement signals having large amplitudes and the frequency of the fall of blood oxygen saturation, as shown in FIG. 5.

Figure 3:
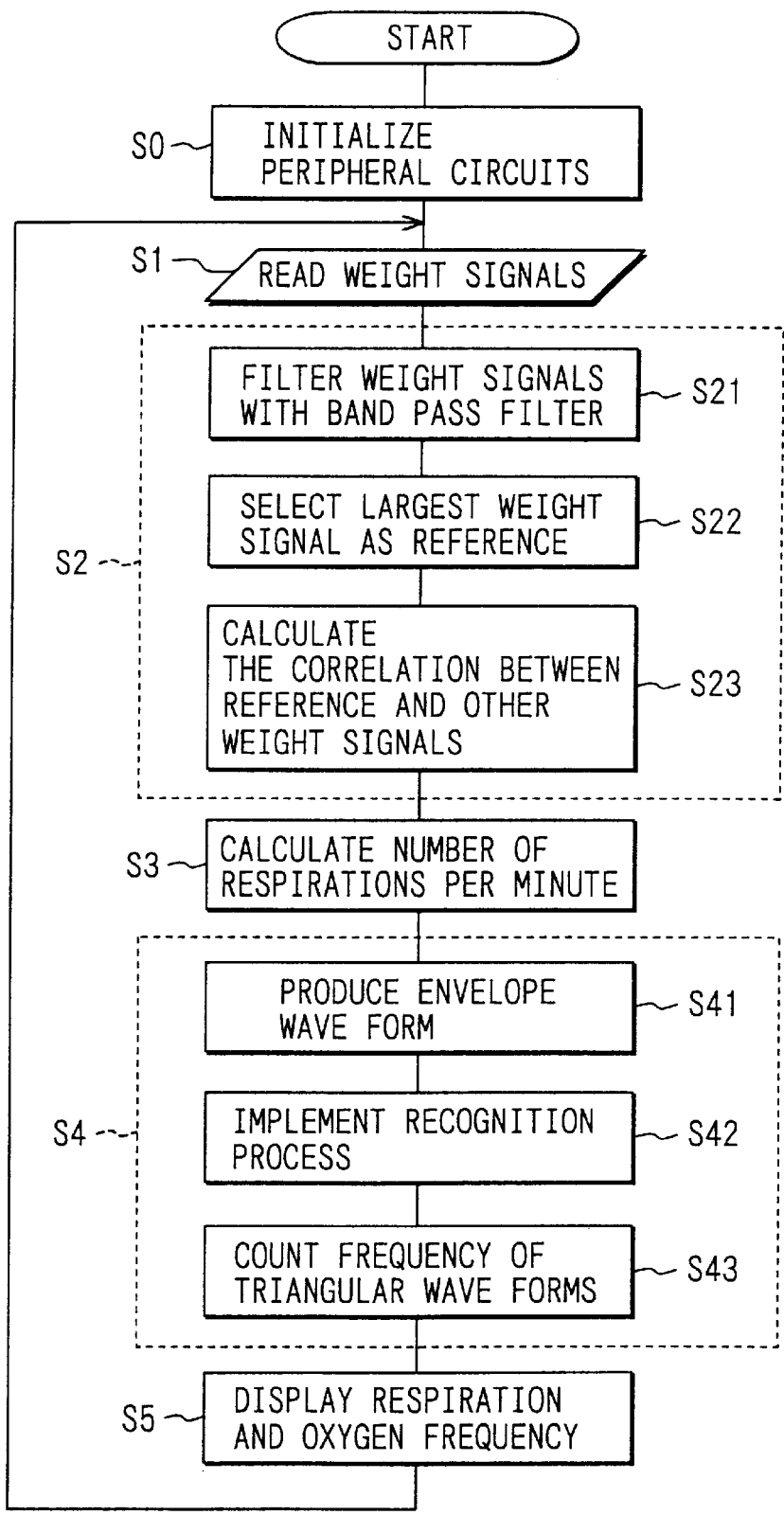
FIG. 3 is a flowchart explaining the operation of a monitoring system according to the present invention.

Next, the operation of the respiration monitoring system 9 for a patient during the occurrence of apnea will be explained with reference to the flowchart of FIG. 3 and the waveform diagram of detected signals shown in FIG. 4. Here, the ECU 34 of the monitoring system calculates the frequency of respiration and the frequency of the fall in blood oxygen saturation according to the flowchart of FIG. 3. The ECU also operates to display the results on display unit 4.

Power is supplied to the power circuit (not shown) of controller 3. Then, the peripheral circuits including the parallel I/O 32 and A/D converter 33 and the RAM area of the ECU 34 are initialized at step S0. In the next step S1, the ECU 34 sequentially reads in weight signals produced by the 210 pressure sensitive elements 21. In steps S2 (steps S21 to S23), the ECU 34 produces a respiratory body movement signal from the variation of weight distribution which is attributable to the vertical movement of the diaphragm caused by the respiration of the sleeping patient.

In step S21, a band-pass filter which is tuned to a certain frequency band adapted to the human respiratory movement is used to filter the signals from the pressure sensitive elements 21. The filtered signals are rendered the frequency analysis (which is called "FFT analysis") to thereby calculate the power spectrum of the frequency band. The pressure sensitive elements 21 that are sensing the respiratory body movement are read based on the magnitude of power spectrum.

In the next step S22, a pressure sensitive element 21 which produces a weight signal of the largest power spectrum of the frequency band (i.e., the largest weight variation), is selected as the reference sensor for the calculation of a respiratory body movement signal.

The measurement frequency band is set slightly wider than the normal human respiration band (15–20 times per minute) so as to cover abnormal respiration states. Specifically, for example, the frequency band 0.25–0.33 Hz for normal respiration is widened to 0.15–0.55 Hz to cover abnormal respiration states of 9–33 times per minute.

In the next step 23, the ECU 34 calculates the mutual correlation between the weight signal of the reference sensor and the weight signals of other pressure sensitive elements 21. Also, here, the ECU selects pressure sensitive elements 21 that produce weight signals which are virtually in-phase with the reference sensor signal (i.e., specifically, signals with phase differences within a ±⅛ period from the reference sensor signal). The ECU 34 sums the weight signals of the selected pressure sensitive elements 21 and the reference sensor signal to produce a summed respiratory body movement signal. The summed respiratory body movement signal does not contain the influence of body movements caused by other reasons besides respiration, and it indicates the state of respiration accurately.

Based on the foregoing process, the respiration signal indicates the frequency of respiration in the range from 9 to 33 times per minute. At the occurrence of apnea or in a state of abnormal respiration outside the prescribed respiration frequency range, the respiratory body movement signal, which represents the frequency of respiration, will not be obtained. The reference sensor will not be determined or the summed respiratory body movement signal will be too small in magnitude, in which cases however it is possible to determine the abnormality of respiration by the detection of these affairs.

FIG. 6 shows an example of the phase relation among the weight signals produced by all pressure sensitive elements 21 indicated by small circles in response to the respiration of the sleeping patient. Here, pressure sensitive elements that produce weight signals, which vary in response to the respiration, are indicated by hatched circles or filled circles. The pressure sensitive element selected as the reference sensor is indicated by a filled square at the right-hand position of the chest.

The pressure sensitive elements indicated by filled circles produce weight signals that are virtually in-phase with the reference sensor signal. However, the pressure sensitive elements indicated by hatched circles produce weight signals which are virtually opposite in phase to the reference sensor signal (i.e., specifically, signals have phase differences of a ⅜ to ⅝ period from the reference sensor signal.)

FIG. 6 reveals that the pressure sensitive elements located in the chest area produce weight signals which are virtually in-phase with the weight signal of the reference sensor. Alternatively, the pressure sensitive elements located in the head area and abdomen area produce weight signals which are virtually opposite in phase to the reference sensor signal. Accordingly, simply summing these weight signals results merely in a mixture of in-phase and opposite-phase weight signals, and does not provide a respiratory body movement signal that correctly indicates the state of respiration.

Accordingly, by selecting pressure sensitive elements that produce weight signals which are virtually in-phase with the reference sensor signal and summing the weight signals of the selected elements and the weight signal of the reference sensor, a respiratory body movement signal which indicates the state of respiration accurately can be obtained. As an alternative to calculating the respiratory body movement signal, pressure sensitive elements that produce weight signals which are virtually opposite in phase to the reference sensor signal are selected and inverted. Here, the signals are phase inverted (phase shift by 180°) and added to the reference sensor signal.

As an alternative to the above described calculation, the reference sensor signal, the virtually in-phase weight signals and inverted versions of virtually opposite-phase weight signals are summed.

In step S3, the ECU 34 calculates the number of respirations per minute from the respiratory body movement signal obtained in the above process. Specifically, it compares the respiratory body movement signal with a certain respiration threshold level TH, and counts the excess signal over the threshold level TH per minute. In steps S4 (steps S41 to S43), the ECU 34 calculates the frequency of the fall in blood oxygen saturation from the respiratory body movement signal calculated in the steps S2.

Initially, in step S41, the ECU 34 produces an envelope waveform that connects peaks of the alternating respiratory body movement signal, as shown in FIG. 4 as a magnified view of FIG. 4. The respiratory body movement signal tends to increase its amplitude in response to aleviation of throat choking. Therefore, the resulting envelope waveform correlates with the fall of blood oxygen saturation, and it exhibits a virtually triangular shape when throat choking is aleviated.

In step S42, the ECU 34 implements the recognition process for the envelope waveform of the respiratory body movement signal, thereby detecting the appearance of a virtually triangular waveform. In step S43, the ECU 34 counts the frequency of the appearance of triangular waveforms as the frequency of the fall of blood oxygen saturation. In step S5, the ECU 34 displays the frequency of respiration and the frequency of the fall in blood oxygen saturation calculated in the steps S3 and S4 numerically or graphically along the time axis on the display unit 4.

In another aspect of the present invention, pressure sensitive elements that produce weight signals virtually opposite in phase (phase-shifted by 180°) are selected to the reference sensor signal and summed with the reference sensor signal to obtain the summed respiratory body movement signal. This is different than the previous method, where pressure sensitive elements that produce weight signals which are virtually in-phase with the reference sensor signal are selected and all these weight signals are summed to obtain the summed respiratory body movement signal.

A still alternative manner of the calculation of respiratory body movement signal is to sum the reference sensor signal and both of virtually in-phase weight signals and inverted versions of virtually opposite-phase weight signals.

The weight sensor is not limited to sensing pressure, but may use any other type of sensor. Such sensors can include static capacitance sensors and strain gauges, which detect weights at multiple points along the sleeping pad. Moreover, the number of sensors is not limited to 210, but instead is arbitrary. A single weight sensor having a relatively wide weight sensing area may be used to produce the respiratory body movement signal.

In another aspect of the invention, the respiration frequency and the frequency of the fall in blood oxygen saturation are displayed on the display unit 4 of the system. This output data may be displayed in a window established on an existing display device, such as a TV screen. Data representing the respiration frequency and frequency of the fall in blood oxygen saturation may be stored on a recording medium for use by a doctor in diagnosis. Alternatively, the data may be sent to a hospital or the like over a public communication line.

In another aspect of the invention, pronounced variation patterns of respiratory body movement are detected. By detecting these patterns, the fall in blood oxygen saturation can be accurately determined. Specifically, falling blood oxygen saturation is determined based on detecting a signal variation pattern where the respiratory body movement signal has its peak maintained below a first threshold value for a certain time length and thereafter exceeds a second threshold value (greater than the first threshold value).

Even during obstructive apnea, the sleeping patient continues breathing. However, the patient's lung does not receive oxygen. Accordingly, there is a body movement indicating respiration (movement of diaphragm), and the respiratory body movement signal is calculated from this movement. The body movement varies little in this state, and the amplitude (peak value) of respiratory body movement signal is also small.

When the blood oxygen saturation falls to the critical level, due to cutoff of oxygen to the lung, the patient breathes very deeply. This action results in a large body movement, creating a large amplitude (peak value) of the respiratory body movement signal. By detecting such a pronounced variation pattern of respiratory body movement signal, the fall of blood oxygen saturation can be accurately determined.

What is claimed is:

1. A respiratory disease monitoring system comprising:
   a detection means which detects body movement of a patient caused by respiration during sleep, wherein the detection means extracts a signal within a frequency band corresponding to a patient' respiratory rate as a respiratory body movement signal;
   a determination means which determines a fall of blood oxygen saturation during an obstructive sleep apnea based on a variation pattern of the body movement detected by the detection means, wherein the determination means recognize, as the fall of blood oxygen saturation, a peak of a maximum amplitude out of peaks of a plurality of waves included in the respiratory body movement signal; and
   an indication means which indicates the fall of blood oxygen saturation.

2. A respiratory disease monitoring system according to claim 1, wherein the determination means determines the fall of blood oxygen saturation based on a body movement variation pattern where the body movement stays below a predetermined level for a predetermined time length and thereafter exceeds the predetermined level.

3. A respiratory disease monitoring system according to claim 1, wherein the detection means includes a plurality of weight sensors arranged beneath, inside or on a surface of a sleeping pad, the sensors producing weight signals representing weights applied to the sensors.

4. A respiratory disease monitoring system according to claim 3, wherein the detection means extracts detection signals having a frequency band of human respiration from weight signals of weight sensors, said detection signals indicative of the respiratory body movement.

5. A respiratory disease monitoring system according to claim 4, wherein the determination means determines the fall in blood oxygen saturation based on the variation pattern of the amplitude of the respiratory body movement signal.

6. A respiratory disease monitoring system according to claim 5, wherein the determination means includes:
   an envelope waveform producing means which produces an envelope waveform which connects peaks of the respiratory body movement signal; and
   a waveform recognition means which recognizes a virtually triangular characteristic waveform that correlates with the fall in blood oxygen saturation and counts frequency of the fall of blood oxygen saturation based on frequency of the appearance of the characteristic waveform.

7. A respiratory disease monitoring system according to claim 6, wherein the indication means indicate the frequency of the fall in blood oxygen saturation in time series.

8. A respiratory disease monitoring system according to claim 4, further comprising a respiration frequency calculating means which calculates the respiration frequency of the sleeping patient based on the respiratory body movement signal, the indication means indicating the respiration frequency of the patient and the fall in blood oxygen saturation.

9. A respiratory disease monitoring system according to claim 3, wherein the detection means includes:
 a reference sensor selecting means which selects as reference sensor a weight sensor that produces a weight signal having a largest amplitude in a respiration frequency band;
 a weight sensor designating means which designates in-phase weight sensors that produce weight signals substantially in-phase with the weight signal produced by the reference sensor and opposite-phase weight sensors that produce weight signals substantially opposite in phase to the weight signal produced by the reference sensor; and
 a respiratory body movement signal producing means which produces a summed respiratory body movement signal based on the weight signal produce reference signals produced sensor and the weight signals produced by the sensor and the weight signals produced by at least one of the in-phase weight sensors and the opposite-phase weight sensors.

10. A respiratory disease monitoring system according to claim 9, wherein the respiratory body movement signal producing means produces a summed respiratory body movement signal by summing the weight signal produced by the reference sensor and the substantially in-phase weight signals, or by summing the weight signal produced by the reference sensor and an inverted version of the substantially opposite-phase weight signals.

11. A respiratory disease monitoring system comprising:
 a detection device having a plurality of sensors disposed under a sleeping area of a patient, each of said sensors outputting signals representative of a force exerted on each said sensor by said patient, wherein the detection device extracts a signal within a frequency band corresponding to a patient's respiratory rate as a respiratory body movement signal; and
 a processing unit which processes each said signal to calculate a fall of blood oxygen saturation during an obstructive apnea, said processing unit calculating said fall in blood oxygen saturation based on a variation pattern of said signals from said plurality of sensors, wherein said processing unit recognizes, as the fall of blood oxygen saturation, a peak of a maximum amplitude out of peaks of a plurality of waves included in the respiratory body movement signal.

12. A respiratory disease monitoring system according to claim 11, wherein a detection device determines the fall of blood oxygen saturation based on a body movement variation pattern where the respiratory body movement stays below a predetermined level for a predetermined time length and thereafter exceeds the predetermined level.

13. A respiratory disease monitoring system according to claim 11, wherein:
 said processing unit selecting a reference sensor that produces a reference signal having a largest amplitude in a respiration frequency band;
 a first portion of said sensors producing signals within a phase range of said reference signal, a second portion of said sensors producing a weight signal outside of said range, said range being substantially in phase with said signal generated by said reference sensor; and
 said processing unit producing a summed respiratory body movement signal based on the reference signal, signals from said first portion of sensors and signals from said second portion of said sensors.

14. A respiratory disease monitoring system according to claim 13, wherein said processing unit sums signals from said first portion, an inverted version of signals from said second portion, and said reference signal to generate said summed respiratory body movement signal.

15. A respiratory disease monitoring system according to claim 13, wherein the processing unit determines the fall in blood oxygen saturation based on the variation pattern of the amplitude of the respiratory body movement signal.

16. A respiratory disease monitoring system according to claim 15, wherein the determination means includes:
 said processing unit connects peaks of the respiratory body movement signal to generate an envelope wave form; and
 said processing unit determines a fall in blood oxygen saturation by identifying a virtually triangular characteristic waveform that correlates with the fall in blood oxygen saturation and counts a frequency of the fall of blood oxygen saturation based on a frequency of the appearance of the characteristic waveform.

17. A method for monitoring a respiratory disease of a patient, comprising the steps of:
 sensing a weight of a patient at a plurality of positions under a sleeping area of said patient to generate a plurality of weight signals from said plurality of positions;
 detecting, as a respiratory body movement signal, a signal within a frequency band corresponding to a patient's respiratory rate from the plurality of weight signals; and
 calculating a fall of blood oxygen saturation during an obstructive apnea based on a wave of a maximum amplitude out of a plurality if waves included in an envelope waveform of a respiratory body movement signal.

18. The method as claimed in claim 17, wherein said calculating step comprises:
 selecting a reference signal having a largest amplitude in a respiration frequency band;
 selecting a first portion of said signals being within a phase range of said reference signal, said range being substantially in phase with said reference signal;
 selecting a second portion of said signals being outside of said phase range of said reference signal; and
 summing a respiratory body movement signal based on said reference signal, signals from said first portion of sensors and signals from said second portion of said sensors.

19. The method as claimed in claim 18, wherein said summing step comprises:
 summing signals from said first portion, an inverted version of said signals from said second portion and said reference to generate said summed respiratory body movement signal.

20. A respiratory disease monitoring system comprising:
 a detection means which detects the body movement of a patient caused by respiration during sleep, wherein the detection means extracts a signal within a frequency band corresponding to a patient's respiratory rate as a respiratory body movement signal;

a determination means which determines a fall of blood oxygen saturation during an obstructive apnea based on a variation pattern of the body movement detected by the detection means, wherein the determination means further comprises, an envelope waveform producing means which produces an envelope waveform which connects peaks of the respiratory body movement signal; and a waveform recognition means which recognizes a characteristic waveform that correlates with the fall in blood oxygen saturation in the envelope waveform, wherein a determination means counts the frequency of the fall of blood oxygen saturation based on a frequency of the appearance of the characteristic waveform; and a display means which displays the fall of blood oxygen saturation.

21. A respiratory disease monitoring system comprising:

a detection means which detects body movement of a patient caused by respiration during sleep, wherein the detection means extracts a signal within a frequency band corresponding to a patient's respiratory rate as a respiratory body movement signal;

a determination means which determines a fall of blood oxygen saturation during an obstructive apnea based on a variation pattern of the body movement detected by the detection means, wherein the determination means comprises a waveform recognition means which recognizes a characteristic waveform, which correlates with the fall in blood oxygen saturation, in peaks of a plurality of waves included in the respiratory body movement signal and wherein the determination means counts a frequency of the fall of blood oxygen saturation based on a frequency of the appearance of the characteristic waveform; and a display means which displays the fall of blood oxygen saturation.

22. A respiratory disease monitoring system comprising:

a detection device having a plurality of sensors disposed under a sleeping area of a patient, each of said sensors outputting signals representative of a force exerted on each said sensor by said patient; and a processing unit which processes each said signal to calculate a fall of blood oxygen saturation during an obstructive apnea, said processing unit calculating said fall in blood oxygen saturation based on a variation pattern of said signals from said plurality of sensors, wherein, said processing unit selecting a reference sensor that produces a reference signal having a largest amplitude in a respiration frequency band;

a first portion of said sensors producing signals within a phase range of said reference signal, a second portion of said sensors producing a weight signal outside of said range, said range being substantially in phase with said signal generated by said reference sensor; and said processing unit producing a summed respiratory body movement signal based on the reference signal, signals from said first portion of sensors and signals from said second portion of said sensors.

23. A respiratory disease monitoring system according to claim 22, wherein said processing unit sums signals from said first portion, an inverted version of signals from said second portion, and said reference signal to generate said summed respiratory body movement signal.

24. A respiratory disease monitoring system according to claim 22, wherein the processing unit determines the fall in blood oxygen saturation based on the variation pattern of the amplitude of the respiratory body movement signal.

25. A respiratory disease monitoring system according to claim 24, wherein the determination means includes:

said processing unit connects peaks of the respiratory body movement signal to generate an envelope wave form; and said processing unit determines a fall in blood oxygen saturation by identifying a virtually triangular characteristic waveform that correlates with the fall in blood oxygen saturation and counts a frequency of the fall of blood oxygen saturation based on a frequency of the appearance of the characteristic waveform.

* * * * *